United States Patent [19]

Vickery

[11] Patent Number: 4,803,981

[45] Date of Patent: Feb. 14, 1989

[54] ANAESTHESIA MASK

[76] Inventor: Ian M. Vickery, The Laurels, 42 Grange Court Road, Westbury-on-Trym, Bristol BS94DR, England

[21] Appl. No.: 715,826

[22] Filed: Mar. 25, 1985

Related U.S. Application Data

[63] Continuation-in-part of Ser. No. 420,803, Sep. 21, 1982, abandoned.

[30] Foreign Application Priority Data

Sep. 22, 1981 [GB] United Kingdom ............... 8128614

[51] Int. Cl.$^4$ .............................................. A62B 9/00
[52] U.S. Cl. .......................... 128/206.24; 128/207.13; 128/207.11
[58] Field of Search ............... 128/203.29, 204.18, 128/206.18, 206.21, 206.24, 206.25, 206.28, 205.25, 207.13, 910

[56] References Cited

U.S. PATENT DOCUMENTS

| | | | |
|---|---|---|---|
| 731,973 | 6/1903 | Teter | 128/207.13 |
| 815,516 | 3/1966 | Coburn | 128/207.13 |
| 1,081,745 | 12/1913 | Johnston | 128/207.13 |
| 1,206,045 | 11/1916 | Smith | 128/206.24 |
| 1,287,149 | 12/1918 | Walter et al. | 128/207.13 |
| 2,241,535 | 5/1941 | Boothby et al. | 128/207.13 |
| 2,254,854 | 9/1941 | O'Connell | 128/207.13 |
| 2,435,653 | 2/1945 | Mauer | 128/207.13 |
| 3,799,164 | 3/1974 | Rollins | 128/910 |
| 4,265,239 | 5/1981 | Fischer, Jr. et al. | 128/910 |
| 4,298,218 | 2/1981 | Fischer | 128/910 |

FOREIGN PATENT DOCUMENTS

| | | | |
|---|---|---|---|
| 21253 | 2/1978 | Australia | 128/205.19 |
| 701696 | 3/1937 | Fed. Rep. of Germany | 128/207.13 |
| 2244887 | 2/1972 | Fed. Rep. of Germany | 128/206.21 |
| 23510 | 10/1910 | United Kingdom | 128/207.13 |
| 20519 | 6/1915 | United Kingdom | 128/203.29 |
| 2045092 | 10/1986 | United Kingdom | 128/206.21 |

Primary Examiner—Edward M. Coven
Assistant Examiner—K. M. Reichle
Attorney, Agent, or Firm—Larson and Taylor

[57] ABSTRACT

A mask for relative analgesia and anaesthesia is moulded from polymeric foam and fits over the nose of the patient, with lateral ports for inlet and outlet of gases. The periphery of the mask has a lower region which bears upon the base of the upper lip, an upper region which contacts the nasal bones, and lateral regions which contact the nasal processes of the maxilla and the maxilla itself and meeet the lower region at the points where the base of the upper lip meets the nasolabial grooves. Certain parts of the face-contacting surfaces are inwardly chamfered.

9 Claims, 3 Drawing Sheets

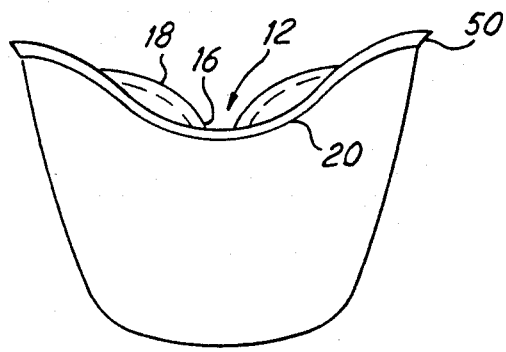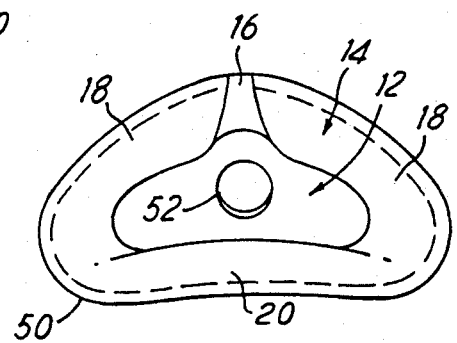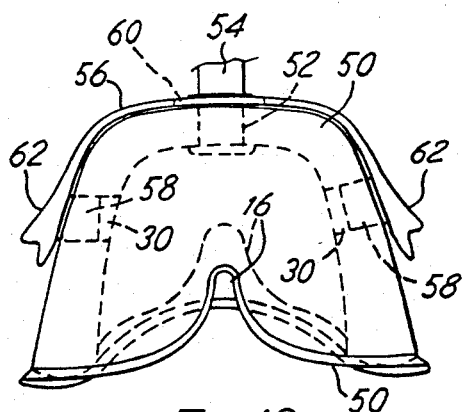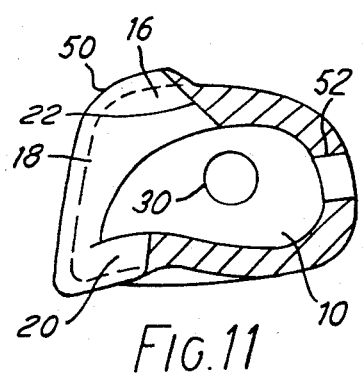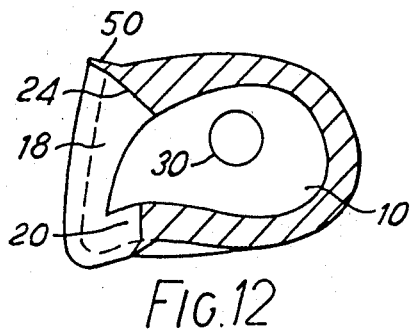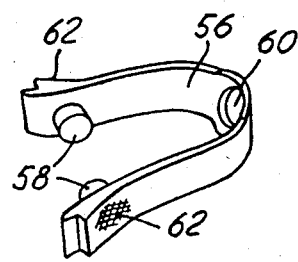

ANAESTHESIA MASK

This application is a continuation-in-part of Application Ser. No. 420803, filed Sept. 21, 1982, now abandoned.

FIELD OF THE INVENTION

This invention relates to masks for administering anaesthetic gases to a patient. More particularly, the invention relates to nasal masks which are intended to administer gas only to the nose of the patient, as distinct from facial masks which cover both the nose and mouth of the patient. The invention is especially applicable to the field of relative analgesia, but is also applicable to general anaesthesia.

BACKGROUND OF THE INVENTION

Relative analgesia is a form of conscious sedation produced by the administration of anaesthetic gas at a level insufficient to produce complete anaesthesia but sufficient to suppress the gag reflex. By this means a throat pack can be inserted into the patient's mouth so as to obstruct the oro-pharyngeal region during surgical or dental work in the patient's mouth. The anaesthetic gases normally used are a mixture of nitrous oxide and oxygen, but other anaesthetic gases could be used in other situations. In any event, the escape of anaesthetic gases into the surrounding atmosphere of the surgery or theatre is a considerable problem, as it can have noticeable effects on the skilled personnel in attendance, and the possible long term effects to such people of continual exposure to such gases is giving rise to some concern.

Conventional nasal masks are of various types. In one type the mask is provided around its face-contacting periphery with a pneumatic cuff. This is intended to be deformable so as to adapt to the facial contours of different patients. However, in practice the cuff has rather limited deformability, and moreover tends to be uniformly deformable as a result of its being a continuous inflated envelope, and hence it does not take account of the fact that there is much more variation in shape and dimensions of some facial areas, as compared with others. As a result, there is usually a very imperfect seal against the patient's face, and a considerable escape of gas results.

An example of this type of mask is the Goldman nasal inhaler (see "Aids to Anaesthesia" by Victor Goldman, published Bailliere, Tindall & Cox, London, 1948, especially at pages 98 and 99).

Another form of conventional mask does not have a pneumatic cuff, but is simply a resilient moulded rubber or plastics shape which is intended to fit closely around the nose of the patient, and whose periphery is intended to be sufficiently flexible so as to accommodate different facial shapes and dimensions in the area contacted. In practice, however, it is found that insufficient regard is paid to the greater variation of facial shapes and dimensions in some parts of the face as compared with others, and again leakage is commonly experienced. Moreover, the mask has to be held firmly against the face to minimise leakage, and is easily displaced by pressure applied to the gas inlet and outlet conduits which are located one on each side of the mask. Examples of such masks are shown in U.S. Pat. No. 1,287,149 (Walter et al), U.S. Pat. No. 2,241,535 (Boothby et al), U.S. Pat. No. 3,799,164 (Rollins) and U.S. Pat. No. 4,248,218 (Fischer). A mask resembling that of Rollins, above, is currently manufactured by Fraser Sweatman Inc., in the United States. A modification of this second type of mask is the "Brown scavenging mask", currently marketed by Narco McKesson in the United States, and includes an outer shell surrounding the mask and connected to vacuum, in an attempt to scavenge leaking gas along with exhaled gas. A third type of mask has been proposed in DE OLS 2244887 (Gmahle), where the mask is made of polymeric foam material, with a central opening for inlet and outlet of gas, and an inset reinforcement around the opening. The reinforcement extends only part way towards the face-contacting region of the mask, the latter region being formed with a thick bead of rounded cross-section, intended to form a seal against the face. No other detail is given as to the mask's shape or intended mode of use, and it is not known whether this mask was intended for anaesthesia (it is referred to as a "respiration mask"), or whether it was ever made at all. At any rate, it seems likely that it was intended to have a generally circular face-contacting opening, and to cover both the nose and the mouth, probably for the administration of oxygen (where of course leakage of gas from the mask is normally of little importance).

Another feature of conventional masks concerns the shape of their face-contacting openings. Nasal masks as currently manufactured seem all to have a high and narrow shape to this opening, somewhat bulbous towards the bottom to accommodate the base of the nose, the top of the mask extending high on the bridge of the nose, or even to the base of the forehead. Most of the above-identified prior art masks are of this kind. An exception appears to be the mask of Walter et al, which appears to have a circular face-contacting opening for both the facial and nasal masks, albeit with an indentation to receive the nose, and, in the case of the facial mask, a slight recess to accommodate the curvature of the chin.

SUMMARY OF THE INVENTION

The present invention adopts a totally new approach to the design of a nasal mask. To begin with, it is based upon extensive research on the dimensions and facial contours of people of different ages, races and sex, to note the extent of such variations in dimension and contour, and hence to relate the characteristics of the mask to these findings. Secondly, the mask is specifically intended to minimise leakage, and provide a standard, hitherto unobtained, which will meet the growing concern about environmental pollution in general, and operator health and safety in particular. This is an acknowledged problem with all conventional anaesthesia masks.

Based upon the research findings, the present mask has a totally different shape to its face-contacting opening from all other masks which have been previously devised. More particularly, it comes lower down on the nose and spreads further out on the sides of the face; the latter being regions which, if they were given any consideration at all, were presumably either thought to be irrelevant or to be subject to too much variation in shape to enable a mask to be satisfactorily applied in these areas. Surprisingly, the inventor has found that, by making the mask out of thick-walled resliently squashable polymeric foam material, and by carefully dimensioning and contouring the face-contacting surfaces, a single mask can be provided which not only provides a greatly improved seal against the face, even in these lateral regions, but will do so in the vast majority of patients, regardless of age, race or sex.

The invention more particularly provides an anaesthesia mask comprising a relatively thick-walled resiliently compressible polymeric foam moulding having an opening to receive the nose of the patient, the opening being bounded by face-contacting surfaces of substantial width, lateral ports being provided in the sides of the foam moulding for the inlet and outlet of gases, the region of the foam moulding forming the periphery of the mask around the opening being resiliently compressible and shaped so as to have a lower region adapted to bear upon the base of the upper lip, an upper region adapted to contact the inferior region of the nasal bones, and lateral regions joining the upper and lower regions, the lateral regions being shaped so as to contact the nasal processes of the maxilla and the maxilla itself, and to meet the lower region where the lateral aspects of the upper lip meet the naso-labial grooves so that portions of the face-contacting surfaces extend at least over said naso-labial grooves, said face-contacting surfaces being shaped to provide a squashable seal around said periphery and thus in the region of said naso-labial grooves, the face-contacting surfaces which contact the inferior and lateral surfaces of the nasal bones and the maxilla on either side of the nose being chamfered inwardly with respect to the interior of the mask.

If the mask is made of highly squashable material, a substantially rigid reinforcement is preferably located between said ports in the region of the mask opposite said opening. The mask may, however, be made of somewhat less squashable material, with a resiliently deflectable flange formed from the material around the face-contacting opening and angled outwardly away from the centre of the mask and towards the face of the wearer.

Other details and advantages of the invention will become apparent from the following detailed description and accompanying drawings.

BRIEF DESCRIPTION OF THE DRAWINGS

FIGS. 8 to 12 show view similar to those of FIGS. 1 to 5 respectively of a second embodiment of mask, and FIG. 13 is a perspective view of an adaptor clip for use with the second embodiment of mask.

Figure 5:
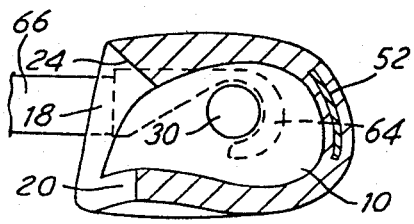
Figure 6:
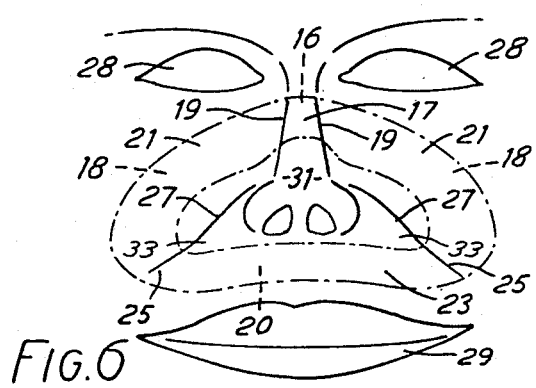
FIG. 6 shows the areas of the face which are contacted by the mask in use.

Referring to the drawings and firstly to FIGS. 1 to 7; the mask is moulded from resiliently flexible polyurethane foam or similar polymeric foamed material, and has a cavity 10 to receive the nose of the patient, the cavity having an opening 12 bounded by a face-contacting edge surface 14. The shape of this surface, as shown in FIGS. 1 to 5, can be defined in relation to the areas of the face which are to be contacted by it, as shown in FIG. 6. At the top of the mask the surface 14 is formed as a tapering recess 16 which seats around the nasal bones 17. This upper region 16 merges into lateral regions 18 which seat upon the nasal processes 19 of the maxilla and on the maxilla 21 itself. A lower region 20 of the surface 14 seats upon the base of the upper lip 23, and merges with the lateral regions 18 over the points 25 where the base of the upper lip meets the naso-labial grooves 27. Thus, the mask does not obstruct the eyes 28 nor the mouth 29, but encloses the nose 31 and the alar base 33 on each side of the nose. As can be seen best in FIGS. 4 and 5, the apex of the upper region 16 of the surface 14, and also the lateral surfaces 18 are chamfered inwardly, as indicated at 22 and 24 respectively. This not only conforms more readily to the shape of the face in those regions, but also allows a greater degree of deformability of the mask in these regions, where it has been found that the greater variations in facial dimensions between patients occur. Moreover, it allows this deformation to be produced without applying undue pressure to the mask, and hence undue discomfort to the patient or undue risk of leakage if the pressure changes.

Figure 1:
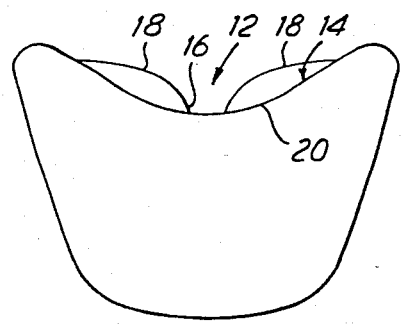
FIG. 1 shows a plan view from below of one embodiment of the mask.
Figure 2:
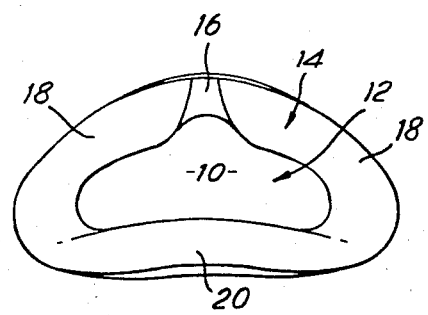
FIG. 2 shows a rear view of the mask on the facial opening thereof.
Figure 3:
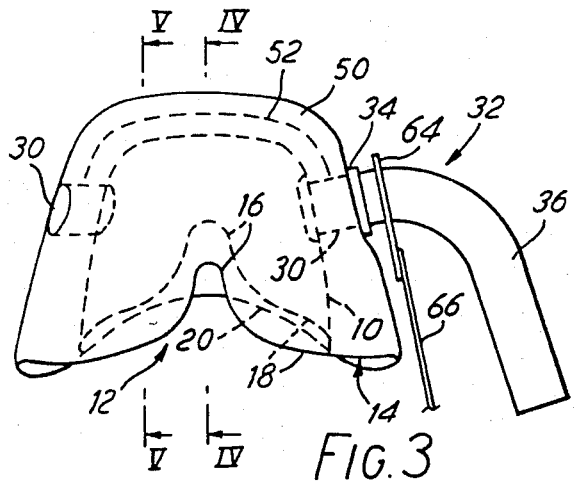
FIG. 3 shows a plan view from above of the mask.
Figure 4:
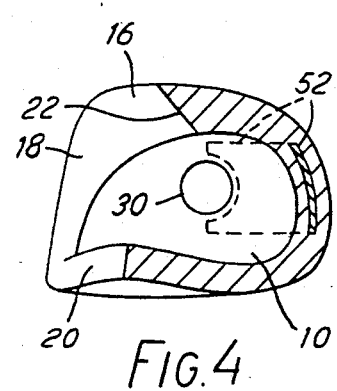
FIGS. 4 and 5 show cross-sectional side views of the mask on the lines IV—IV and V—V.

The mask is provided with two lateral ports 30 into which are fitted gas inlet and outlet connectors 32. Each connector comprises an adaptor portion 34 and an elbow portion 36. The adaptor portion 34 is a straight sleeve with axially spaced apart flanges between which is received and compressed somewhat the region of the mask around the port 30, as shown in FIG. 3. FIG. 3 only shows one connector fitted, but another similar connector is fitted to the other port 30. The elbow part 36 projecting from the mask can be push fitted into a flexible hose for gas supply or removal. With the connectors 32 thus fitted to the mask, either of the elbow portions can be rotated without disturbing the mask. This enables the hoses to be readily moved by the surgeon with little risk of displacing the mask and allowing leakage of gas.

Figure 7:
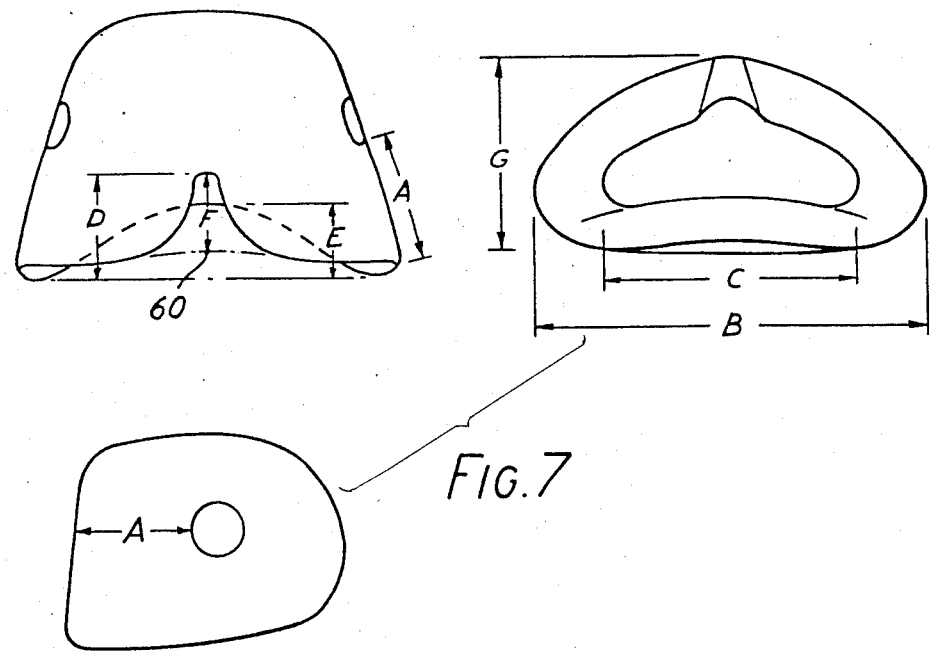
FIG. 7 shows plan, rear and side views of the mask marked for the purpose of indicating some of the dimensions thereof.

The front portion 50 of the mask is provided with a substantially rigid insert 52, which is conveniently moulded from polypropylene sheet material. As can be seen from FIGS. 3 and 4, the insert extends across the front portion of the mask and around the side portions until it terminates just short of the ports 30. This insert enables light pressure to be applied to the mask towards the face to ensure that a satisfactory seal is maintained between the mask and the face. The ends of the insert bear upon the gas inlet and outlet connectors 32, so that essentially the front portion of the mask is not distorted by this pressure, and the distortion only occurs in the region of the face contacting surface 14. As well as the shape of the mask, its dimensions are of some importance in achieving applicability to a wide range of patients. The principal dimensions are indicated in FIG. 7 as follows.

A. The shortest distance on the outside surface of the mask from the port 30 to the nearest point on the face contacting edge 14 is about 27 mm. This is quite important in providing sufficient compressibility at this point, since there can be considerable variation in the facial dimensions of different patients in this region. This dimension should be at least 24 mm, and 27 mm gives a reasonable margin to allow for the more unusual facial shapes.

B and C. The overall external and internal widths respectively of the mask at the facial opening, are about 93 mm and 58 mm respectively.

D. The horizontal distance from the points on the outside surface of the mask where the lateral regions 18 meet the lower region 20 to the apex of the upper region 16 is about 26 mm.

E. The horizontal distance from the points on the outside surface of the mask where the lateral regions 18 meet the lower region 20 and the centre of the lower region 20 is about 19 mm.

F. The distance on the outside surface of the mask from the apex of the upper region 16 and a projected point 60 representing an extension of the outside surface of the lateral regions 18 is about 17 mm. This gives an indication of the forward extension of the upper region 16 as compared with the lateral regions 18.

G. The overall height of the mask is about 48 mm.

The foregoing dimensions B to F are the preferred dimensions for the embodiment shown, and represent about a 10% margin of safety over the ranges of dimensions which have been found from extensive measurements carried out on people of different ages, sexes and races. Thus, this embodiment of mask should fit the vast majority of patients.

FIGS. 3 and 5 also show how a halter can be used with the mask during relative analgesia. A pair of hook-shaped plates 64, suitably made of plastics material, are each connected to respective tapes 66. Each plate 64 is hooked over a respective one of the connectors 32 close to the adaptor portion 34. The tapes 66 are attached to the sides of the face of the wearer by adhesive tape. It will be noted that, because of the unique design and construction of the mask of the present invention, the mask can be securely held to the face of the patient by means of these halter tapes, while allowing the connectors 32 to be freely rotated with respect to the mask, thereby making it possible for the oral surgeon to obtain access to the patient's mouth.

The mask as described and illustrated above is made of highly squashable material, suitably polyurethane foam, optionally provided with a gas-impermeable infrared skin surface and to give it sufficient rigidity where required, the insert 52 is provided. In the embodiment shown in FIGS. 8 to 12, however, the mask can be made of a material which is somewhat less squashable, for example a closed cell polyurethane foam formed wit an integral skin on its surface. This construction with an integral skin effectively prevents gas from seeping through the foam material. However, to compensate for the somewhat lower degree of squashability, a flange 50 is provided around the face-contacting opening of the mask. This flange is angled outwardly with respect to the mask and towards the face of the wearer, and is resiliently deflectable on contact with the face of the wearer. The flange thus compensates for the lower degree of squashability, and establishes face contact where it may not be made by the main face-contacting surface 14. The width of the flange 50 varies from about 2 mm in the lateral regions of the mask where the facial variations are greatest, to about 1 mm or less in the central region of the mask around the nose and upper lip.

The mask is also shown with a front port 52, which is provided if it is to be used for general anaesthesia, as opposed to relative analgesia. (For relative analgesia this front port can be omitted.) In general anaesthesia the gas is normally supplied through an inlet duct at the front of the mask, and removed by an outlet duct coaxially located within the inlet duct. Thus, there is only need for one opening in the mask in such a case. The ports 30 are plugged by a U-shaped clip 56, as shown in FIG. 13, conveniently made of rigid plastics material, so as to fit over the front of the mask, and having a pair of plugs 58 near its free ends which enter the openings 30 in the mask. The clip is provided with a central opening 60 to register with the opening 52 in the mask, so that the single gas inlet/outlet connector 54 can be attached. The outside surfaces of the clip at its free ends are also provided with formations 62 shaped to receive the thumbs of the anaesthetist when he is holding the mask onto the face of the patient being anaesthetised.

The embodiment of mask shown in FIGS. 1 to 7 can also be modified to provide a third opening 52, for which purpose a plug 54 or clip 56 is employed.

I claim:

1. A component for an anaesthesia mask comprising a relatively thick-walled resiliently compressible polymeric foam moulding having an opening to receive the nose of the patient, the opening being bounded by face-contacting surfaces of substantial width, lateral ports being provided in the sides of the foam moulding for the inlet and outlet of gases, the region of the foam moulding forming the periphery of the mask around the opening being resiliently compressible and shaped so as to have a lower region adapted to bear upon the base of the upper lip, an upper region adapted to contact the inferior region of the nasal bones, and lateral regions joining the upper and lower regions, the lateral regions being shaped so as to contact the nasal processes of the maxilla and the maxilla itself, and to meet the lower region where the lateral aspects of the upper lip meet the nasolabial grooves so that portions of the face-contacting surfaces extend at least over said naso-labial grooves, said face-contacting surfaces being shaped to provide a squashable seal around said periphery and thus in the region of said naso-labial grooves, the face-contacting surfaces which contact the inferior and lateral surfaces of the nasal bones and the maxilla on either side of the nose being chamfered inwardly with respect to the interior of the mask.

2. An anaesthesia mask component according to claim 1 which incorporates a substantially rigid reinforcement located between said ports in the region of the mask opposite said opening.

3. An anaesthesia mask component according to claim 1 wherein the distance over the outside surface of the mask between said gas inlet and outlet ports and the nearest point thereto of lateral face-contacting regions is at least 24 mm.

4. An anaesthesia mask component according to claim 3 wherein said distance is at least 27 mm.

5. An anaesthesia mask component according to claim 1 wherein the gas inlet and outlet ports take the form of apertures in the sides of the mask for receiving respective inlet and outlet connectors.

6. An anaesthesia mask component according to claim 5 in combination with inlet and outlet connectors received in said apertures, each connector comprising a short adaptor sleeve portion fitted into a said aperture and having axially spaced apart flanges which receive therebetween and compress somewhat the material of the mask around the aperture, and an elbow shaped portion joined to the adaptor sleeve portion and projecting from the mask and rotatable relative to the mask, the end of the elbow portion remote from the adaptor sleeve portion being adapted for fitting to a gas transfer hose.

7. An anaesthesia mask component according to claim 1 provided with a gas-impermeable integral skin surface.

8. An anaesthesia mask component according to claim 7 wherein the mask is made from closed cell polymeric foam material.

9. An anaesthesia mask component according to claim 8 wherein the mask has an integral resiliently deflectable flange around said face-contacting surfaces of the mask, the flange being angled outwardly from the centre of the mask and towards the face of the wearer.

* * * * *